United States Patent
Yoshida

(10) Patent No.: US 10,538,503 B2
(45) Date of Patent: Jan. 21, 2020

(54) METHOD FOR PRODUCING 3-METHYL-2-THIOPHENECARBOXYLIC ACID

(71) Applicant: ISHIHARA SANGYO KAISHA, LTD., Osaka (JP)

(72) Inventor: Tatsunori Yoshida, Osaka (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 0 days.

(21) Appl. No.: 16/342,086

(22) PCT Filed: Oct. 24, 2017

(86) PCT No.: PCT/JP2017/038371
§ 371 (c)(1),
(2) Date: Apr. 15, 2019

(87) PCT Pub. No.: WO2018/079553
PCT Pub. Date: May 3, 2018

(65) Prior Publication Data
US 2019/0248759 A1    Aug. 15, 2019

(30) Foreign Application Priority Data

Oct. 26, 2016 (JP) .................. 2016-209484

(51) Int. Cl.
*C07D 333/38* (2006.01)
*C07D 333/40* (2006.01)

(52) U.S. Cl.
CPC .................. *C07D 333/40* (2013.01)

(58) Field of Classification Search
CPC .................................... C07D 333/40
USPC .......................................... 549/71
See application file for complete search history.

(56) References Cited

U.S. PATENT DOCUMENTS

| 3,741,984 A | 6/1973 | Sheeran |
| 2001/0006975 A1 | 7/2001 | Wood et al. |
| 2007/0179143 A1 | 8/2007 | Kim et al. |
| 2011/0112311 A1 | 5/2011 | Ando et al. |

FOREIGN PATENT DOCUMENTS

| JP | 2001-247563 A | 9/2001 |
| JP | 2002-500650 A | 1/2002 |
| JP | 2007-520422 A | 7/2007 |
| WO | 2009/157525 A1 | 12/2009 |
| WO | 2016/161063 A1 | 10/2016 |

OTHER PUBLICATIONS

Koji Nemoto et al., "Direct Carboxylation of Thiophenes and Benzothiophenes with the Aid of EtAlCl2", Bulletin of the Chemical Society, Mar. 3, 2012, pp. vol. 85, No. 3, 369-371.
International Search Report dated Dec. 12, 2017 in International Patent Application No. PCT/JP2017/038371.
International Preliminary Report on Patentability dated Dec. 12, 2017 in International Patent Application No. PCT/JP2017/038371.

*Primary Examiner* — Taylor V Oh
(74) *Attorney, Agent, or Firm* — Greenblum & Bernstein, P.L.C.

(57) ABSTRACT

To provide a method for producing 3-methyl-2-thiophenecarboxylic acid.
A method for producing 3-methyl-2-thiophenecarboxylic acid, which comprises reacting 3-methylthiophene with chlorosulfonyl isocyanate, and hydrolyzing the obtained reaction product.

12 Claims, No Drawings

METHOD FOR PRODUCING 3-METHYL-2-THIOPHENECARBOXYLIC ACID

TECHNICAL FIELD

The present invention relates to a method for producing 3-methyl-2-thiophenecarboxylic acid useful as an intermediate for producing drugs and agrochemicals.

BACKGROUND ART

Patent Document 1 discloses, as a method for producing 3-methyl-2-thiophenecarboxylic acid, a method for producing 3-methyl-2-thiophenecarboxylic acid which comprises reacting a 3,4-dihalobutan-2-one with a thioglycolic acid in the presence of a base. However, there are problems with industrial application of this method such as the use of malodorous thioglycolic acid.

Further, Patent Document 2 discloses a method for producing 3-methyl-2-thiophenecarboxylic acid which comprises chlorinating 3-methylthiophene to prepare a Grignard reagent of 2-chloro-3-methylthiophene, and reacting the Grignard reagent with carbon dioxide. However, this method requires two reaction steps of the chlorination reaction and the Grignard reaction from 3-methylthiophene, and a dichloro-form is formed as a by-product by the first chlorination reaction. Accordingly, this method should be further improved as an industrial method for producing 3-methyl-2-thiophenecarboxylic acid.

As a more simple method for producing 3-methyl-2-thiophenecarboxylic acid, a method of directly carboxylating 3-methylthiophene may be mentioned. For example, Non-Patent Document 1 discloses a method for directly carboxylating 3-methylthiophene in the presence of a Lewis acid. However, there are problems with industrial application since this method requires use of a Lewis acid such as pyrophoric ethyl aluminum dichloride under pressure conditions. Further, this method is insufficient for industrial application also in view of the yield and the selectivity.

A method of directly carboxylating a thiophene using chlorosulfonyl isocyanate is disclosed in Patent Documents 3 and 4.

However, the method disclosed in Patent Document 3 does not involve a problem of regioselectivity (selectivity for 3-methyl-2-thiophenecarboxylic acid and 4-methyl-2-thiophenecarboxylic acid) in carboxylation of 3-methylthiophene since thiophene is used as a raw material. Further, the yield of the obtainable 2-thiophenecarboxylic acid is not so high as from about 50% to about 75%.

The method disclosed in Patent Document 4 is a method of reacting a thiophene with chlorosulfonyl isocyanate and reacting the reaction product with an amine to obtain a N-sulfamoyl-2-thiophenecarboxamide, not a method for producing a thiophenecarboxylic acid. Further, it failed to specifically disclose an example relating to the reaction of a thiophene with chlorosulfonyl isocyanate.

PRIOR ART DOCUMENTS

Patent Documents

Patent Document 1: JP-A-2001-247563
Patent Document 2: WO2009/157525
Patent Document 3: WO2016/161063
Patent Document 4: U.S. Pat. No. 3,741,984

Non-Patent Document

Non-Patent Document 1: Bulletin of the Chemical Society Japan, Vol. 85, No. 3, 369-371 (2012)

DISCLOSURE OF INVENTION

Technical Problem

The object of the present invention is to provide an efficient method with simple operation for producing 3-methyl-2-thiophenecarboxylic acid useful as an intermediate for producing drugs and agrochemicals, from 3-methylthiophene with high selectivity and high yield.

Solution to Problem

The present inventor has conducted extensive studies to achieve the above object and as a result, found that by a very simple operation of reacting 3-methylthiophene with chlorosulfonyl isocyanate and hydrolyzing the obtained reaction product, 3-methylthiophene can be directly carboxylated selectively at the 2-position without using a pyrophoric Lewis acid, whereby 3-methyl-2-thiophenecarboxylic acid can be obtained with high selectivity and high yield. Further, the method of the present invention is advantageous also in that formation of impurities is very little, whereby purification of 3-methyl-2-thiophenecarboxylic acid is easy.

That is, the present invention provides a method for producing 3-methyl-2-thiophenecarboxylic acid, which comprises step (1) of reacting 3-methylthiophene with chlorosulfonyl isocyanate, and step (2) of hydrolyzing the reaction product obtained in the step (1).

Advantageous Effects of Invention

According to the present invention, 3-methyl-2-thiophenecarboxylic acid useful as an intermediate for producing drugs and agrochemicals can simply and efficiently be produced from 3-methylthiophene with high yield and high selectivity.

DESCRIPTION OF EMBODIMENTS

The method for producing 3-methyl-2-thiophencarboxylic acid of the present invention (hereinafter sometimes referred to simply as the method of the present invention) comprises the following steps (1) and (2):

step (1): reacting 3-methylthiophene with chlorosulfonyl isocyanate;

step (2): hydrolyzing the reaction product obtained in the step (1).

Now, each step will be described in detail below.

The step (1) of the present invention is a step of reacting 3-methylthiophene with chlorosulfonyl isocyanate.

The order of addition of the raw materials in the step (1) is not particularly limited. For example, (a) chlorosulfonyl isocyanate is added to 3-methylthiophene, (b) 3-methylthiophene is added to chlorosulfonyl isocyanate, or (c) 3-methylthiophene and chlorosulfonyl isocyanate are added to the reaction system at the same time or continuously, etc. 3-Methylthiophene and chlorosulfonyl isocyanate may respectively be used as a mixture with a solvent, as the case requires. As a preferred embodiment, procedure (b) of adding 3-methylthiophene to a mixture of chlorosulfonyl isocyanate and a solvent may be mentioned.

In the step (1), the amounts of use of 3-methylthiophene and chlorosulfonyl isocyanate vary depending on e.g. the reaction conditions and cannot generally be defined, however, the amount of chlorosulfonyl isocyanate is preferably from 1 to 5 mol, more preferably from 1 to 1.5 mol per 1 mol of 3-methylthiophene.

The step (1) is carried out usually in the presence of a solvent.

The solvent used in the step (1) is not particularly limited so long as it does not adversely affect the reaction and may, for example, be a halogenated hydrocarbon such as carbon tetrachloride, chloroform, dichloromethane, 1,2-dichloroethane, trichloroethane or chlorobenzene; an aromatic hydrocarbon such as benzene, toluene or xylene (including ortho-xylene, para-xylene, ethylbenzene and their mixture with an optional proportion); a saturated hydrocarbon such as n-paraffin, iso-paraffin or naphthene; an ether such as diethyl ether, dibutyl ether, tetrahydrofuran, tetrahydropyran, 1,4-dioxane, cyclopentyl methyl ether, diethoxyethane or methyl t-butyl ether; a ketone such as acetone, methyl ethyl ketone or methyl isobutyl ketone; a nitrile such as acetonitrile or propionitrile; an ester such as methyl acetate, ethyl acetate or propyl acetate; a nitrogen-containing aromatic compound such as pyridine or quinoline; or an amide such as N,N-dimethylformamide or N,N-dimethylacetamide. As the solvent, one member or two or more members may properly be selected. Further, within a range not to impair the reaction, a solvent other than the above may be used.

Among these solvents, preferred is a halogenated hydrocarbon, an aromatic hydrocarbon, an ester or a ketone. More specifically, preferred is dichloromethane, 1,2-dichloroethane, chlorobenzene, toluene, xylene, ethyl acetate, dibutyl ether or methyl ethyl ketone, more preferred is dichloromethane, toluene, xylene, ethyl acetate or methyl ethyl ketone, further preferred is toluene or xylene.

As the case requires, the solvent may be dehydrated by distillation or with a dehydrating agent before use.

The amount of the solvent in the step (1) varies depending on the amount of the raw materials, the type of the solvent, the reaction conditions, etc. and cannot generally be defined, and is usually from 1 to 30 parts by volume, preferably from 1 to 10 parts by volume per 1 part by weight of 3-methylthiophene. Specifically, in the present invention, the amount of the solvent is from 1 to 30 mL, preferably from 1 to 10 mL per 1 g of 3-methylthiophene.

The reaction temperature and the reaction time in the step (1) vary depending upon the reaction conditions and cannot generally be defined. From the viewpoint of selectivity for the obtainable 3-methyl-2-thiophenecarboxylic acid and 4-methyl-2-thiophenecarboxylic acid, the reaction temperature is preferably from −20 to 150° C., more preferably from 0 to 100° C., further preferably from 0 to 20° C., still more preferably from 0 to 10° C. The reaction time is preferably from 0.1 to 24 hours, more preferably from 0.5 to 10 hours, further preferably from 0.5 to 3 hours.

The step (2) of the present invention is a step of hydrolyzing the reaction product in the step (1).

Hydrolysis may be carried out in accordance with a known method in this technical field and may be conducted, for example, by treating the reaction product in the step (1) with water, a base, an acid, an aqueous base solution or an aqueous acid solution.

After completion of the step (1), a post-treatment operation by a conventional method may be carried out and then the step (2) is carried out. However, from the viewpoint of easiness of operation, the reaction product in the step (1) is preferably subjected to the step (2) as it is without being isolated from the reaction mixture. A specific operation is not particularly limited and may, for example, be such that (a) water, a base, an acid, an aqueous base solution or an aqueous acid solution is added to the reaction mixture of the step (1), (b) the reaction mixture of the step (1) is added to water, a base, an acid, an aqueous base solution or an aqueous acid solution, or (c) the reaction mixture of the step (1) and water, a base, an acid, an aqueous base solution or an aqueous acid solution are added to the reaction system at the same time or continuously to carry out the step (2).

In a case where the reaction mixture in the step (1) is subjected to the step (2) as it is, a step of removing the solvent used in the step (1) may be conducted as the case requires during or after the step (2). Removal of the solvent may be carried out by a conventional method such as azeotropy, distillation under reduced pressure or liquid separation, etc.

The base used in the step (2) may, for example, be an alkali metal hydroxide such as sodium hydroxide or potassium hydroxide, etc.; an alkaline earth metal hydroxide such as magnesium hydroxide or calcium hydroxide, etc.; an alkali metal carbonate such as sodium carbonate or potassium carbonate, etc.; an alkaline earth metal carbonate such as magnesium carbonate or calcium carbonate, etc.; or an alkali metal hydrogen carbonate such as sodium hydrogen carbon or potassium hydrogen carbonate, etc. Among these bases, an alkali metal hydroxide is preferred, and sodium hydroxide or potassium hydroxide is more preferred.

The base to be used in the step (2) may be subjected to the reaction as it is, or may be subjected to the reaction in a state of an aqueous solution. It is preferably subjected to the reaction in a state of an aqueous solution, more preferably in a state of a 40 to 60 wt % aqueous solution.

The acid used in the step (2) may, for example, be an inorganic acid such as hydrochloric acid, hydrobromic acid, phosphoric acid, sulfuric acid or nitric acid; or an organic acid such as acetic acid, formic acid or propionic acid. Among these acids, preferred is hydrochloric acid, hydrobromic acid or sulfuric acid, more preferred is hydrochloric acid or sulfuric acid. Further, an acid formed by treating the reaction product in the step (1) with water may be utilized.

The amount of water, the base or the acid in the step (2) is preferably at least 1 mol, more preferably from 1 to 30 mol, further preferably from 1 to 20 mol per 1 mol of 3-methylthiophene.

The step (2) is carried out usually in the presence of a solvent.

The solvent used in the step (2) is not particularly limited so long as it does not adversely affect the reaction and may, for example, be water; a halogenated hydrocarbon such as carbon tetrachloride, chloroform, dichloromethane, 1,2-dichloroethane, trichloroethane or chlorobenzene; an aromatic hydrocarbon such as benzene, toluene or xylene (including ortho-xylene, para-xylene, ethylbenzene and their mixture with an optional proportion); a saturated hydrocarbon such as n-paraffin, iso-paraffin or naphthene; an ether such as diethyl ether, tetrahydrofuran, tetrahydropyran, 1,4-dioxane, cyclopentyl methyl ether, diethoxyethane, methyl t-butyl ether or dibutyl ether; a ketone such as acetone, methyl ethyl ketone or methyl isobutyl ketone; a nitrile such as acetonitrile or propionitrile; an alcohol such as methanol or ethanol; an acid such as acetic acid; or an amide such as N,N-dimethylformamide or N,N-dimethylacetamide, etc. As a solvent, one member or two or more members may be properly selected. Further, within a range not to impair the reaction, a solvent other than the above may be used, and the same solvent as the solvent used in the step (1) may be used as it is. The water, base, acid, aqueous base solution or aqueous acid solution used in the step (2) may function also as a solvent.

Among these solvents, preferred is water, a halogenated hydrocarbon, an aromatic hydrocarbon or an ether, more preferred is water, dichloromethane, chlorobenzene, toluene, xylene, dibutyl ether or tetrahydrofuran, and further preferred is water, toluene, xylene or a mixture thereof.

The amount of the solvent varies depending upon the amount of the raw materials, the type of the solvent, the reaction conditions, etc. and cannot generally be defined, and is usually from 1 to 50 parts by volume, preferably from 1 to 10 parts by volume per 1 part by weight of 3-methylthiophene. Specifically, in the case of the present invention, the amount of the solvent is from 1 to 50 mL, preferably from 1 to 10 mL per 1 g of 3-methylthiophene.

More specifically, the step (2) preferably comprises step (2-1) of treating the reaction product obtained in the step (1) with water and step (2-2) of treating the reaction product obtained in the step (2-1) with a base. The step (2-1) is carried out preferably under neutral (in the vicinity of pH 7) to acidic (for example, pH 3 or lower, preferably pH 0 to 2) conditions. The step (2-2) is carried out preferably under basic (for example, pH 11 or higher, preferably pH 12 to 14) conditions.

From the viewpoint of easiness of operation, the reaction product in the step (2-1) is preferably subjected to the step (2-2) as it is without being isolated from the reaction mixture. A specific procedure is not particularly limited. After completion of the step (2-1), (a) a base or its aqueous solution is added to the reaction mixture in the step (2-1), (b) the reaction mixture in the step (2-1) is added to a base or its aqueous solution, or (c) the reaction mixture in the step (2-1) and a base or its aqueous solution are added to the reaction system at the same time or continuously to carry out the step (2-2).

In such a manner, the reaction product in the step (1) is treated with water and then with a base to obtain high purity 3-methyl-2-thiophenecarboxylic acid with high yield.

The reaction temperature and the reaction time in the step (2) vary depending upon the reaction conditions, etc., and cannot be generally defined. For example, in a case where hydrolysis is conducted in two stages of the steps (2-1) and (2-2), the reaction temperature in the step (2-1) is preferably from −20 to 120° C., more preferably from −20 to 50° C., further preferably from 0 to 50° C., and the reaction time is preferably from 0.1 to 24 hours, more preferably from 0.1 to 3 hours, further preferably from 0.1 to 1 hour. The reaction temperature in the step (2-2) is preferably from 0 to 150° C., more preferably from 20 to 120° C., and the reaction time is preferably from 0.1 to 24 hours, more preferably from 1 to 10 hours. The solvent contained in the reaction mixture in the step (2) may be removed by azeotropically boiling the reaction mixture. Removal is carried out preferably by heating the reaction mixture to an azeotropic temperature after the base is added in the step (2-2).

In a case where hydrolysis is conducted in two stages of the steps (2-1) and (2-2), after the step (2-1), a corresponding amide compound (3-methyl-2-thiophenecarboxamide) may be obtained. Further by treating the amide compound thus obtained with a base, 3-methyl-2-thiophenecarboxylic acid may be obtained.

In a case where 3-methyl-2-thiophenecarboxylic acid is obtained by hydrolysis in the presence of a base (for example, step (2-2)), 3-methyl-2-thiophenecarboxylic acid forms a salt with the base used, and by treating the salt with an acid such as hydrochloric acid or sulfuric acid, the salt may be converted to 3-methyl-2-thiophenecarboxylic acid. At the time of treatment with an acid, an alcohol (for example, methanol, ethanol, propanol or isopropyl alcohol, etc.) or the like may be added. Further, a salt of 3-methyl-2-thiophenecarboxylic acid (for example, an alkali metal salt such as a sodium salt or a potassium salt, or an alkaline earth metal salt such as a magnesium salt or a calcium salt, etc.) may be obtained without treatment with an acid.

According to the present invention, high purity 3-methyl-2-thiophenecarboxylic acid may be obtained by a simple operation, and as the case requires, the obtained 3-methyl-2-thiophenecarboxylic acid may be isolated by post-treatment by a conventional method such as washing (for example, with water, an alcohol (such as methanol) or an organic solvent (such as toluene) or their mixture (for example, a mixture of water and an alcohol (such as methanol) or an organic solvent (such as toluene)), recrystallization or drying, etc.

In the method of the present invention, various factors can be selected from the above-mentioned examples and conditions properly and combined. That is, the types, forms and amounts of 3-methylthiophene, chlorosulfonyl isocyanate, the solvent and the acid and/or the base; the reaction temperature; the reaction time and the like may be selected properly from usual or preferred examples and conditions and may be combined with one another. Further, a known operation in this technical field, other than the above mentioned operations, such as removal of the solvent, may be combined as the case requires.

Now, preferred embodiments of the present invention are shown below. However, the present invention is not limited thereto.

[1] A method for producing 3-methyl-2-thiophenecarboxylic acid, which comprises step (1) of reacting 3-methylthiophene with chlorosulfonyl isocyanate, and step (2) of hydrolyzing the reaction product obtained in the step (1).

[2] The method according to [1], wherein the step (2) comprises step (2-1) of treating the reaction product obtained in the step (1) with water, and step (2-2) of treating the reaction product obtained in the step (2-1) with a base.

[3] The method according to [2], wherein the base is an alkali metal hydroxide.

[4] The method according to [2], wherein the base is sodium hydroxide.

[5] The method according to any one of [1] to [4], wherein the step (1) is carried out in the presence of a solvent.

[6] The method according to [5], wherein the solvent is one member or two or more members selected from the group consisting of a halogenated hydrocarbon, an aromatic hydrocarbon, an ester and a ketone.

[7] The method according to [5], wherein the solvent is one member or two or more members selected from the group consisting of dichloromethane, 1,2-dichloroethane, chlorobenzene, toluene, xylene, ethyl acetate, dibutyl ether and methyl ethyl ketone.

[8] The method according to [5], wherein the solvent is one member or two or more members selected from the group consisting of dichloromethane, toluene, xylene, ethyl acetate and methyl ethyl ketone.

[9] The method according to [5], wherein the solvent is one member or two or more members selected from the group consisting of dichloromethane, toluene and xylene.

[10] The method according to any one of [1] to [9], wherein the reaction of the step (1) is carried out at from 0 to 20° C.
[11] The method according to any one of [1] to [10], wherein the reaction product obtained in the step (1) is subjected to the step (2) as it is without being isolated from the reaction mixture.
[12] The method according to any one of [1] to [11], wherein in the step [1], the amount of chlorosulfonyl isocyanate is from 1 to 1.5 mol per 1 mol of 3-methylthiophene.
[13] The method according to any one of [2] to [12], wherein the treatment of the step (2-1) is carried out at from 0 to 50° C.
[14] The method according to any one of [2] to [13], wherein the treatment of the step (2-2) is carried out at from 80 to 120° C.
[15] The method according to any one of [1] to [14], wherein after completion of the treatment in the step (2-2), water, an alcohol or both of them are added to the reaction mixture, and then an acid is added to precipitate and purify 3-methyl-2-thiophenecarboxylic acid.
[16] The method according to any one of [1] to [15], wherein after completion of the treatment in the step (2-2), water, ethanol or both of them are added to the reaction mixture, and then concentrated hydrochloric acid is added to precipitate and purify 3-methyl-2-thiophencarbonxylic acid.
[17] The method according to any one of [1] to [16], wherein the step (2) is carried out in the presence of a solvent.
[18] The method according to any one of [1] to [17], wherein the solvent used in the step (2) is one member or two or more members selected from the group consisting of water, dichloromethane, chlorobenzene, toluene, xylene, dibutyl ether and tetrahydrofuran.
[19] The method according to any one of [1] to [18], wherein in the step (1), 3-methylthiophene is added to a solution containing chlorosulfonyl isocyanate.

Now, examples of the present invention will be described. However, it should be understood that the present invention is by no means restricted thereto.

Abbreviations in the following examples are as follows.
3-MT: 3-Methylthiophene
3-MTCA: 3-Methyl-2-thiophenecarboxylic acid
4-MTCA: 4-Methyl-2-thiophenecarboxylic acid
NaOH: Sodium hydroxide

EXAMPLES

Example 1

Step 1
Into a four-necked flask equipped with a stirrer, a thermometer, a condenser tube and a dropping funnel, 3-MT (5.9 g) and dichloromethane (30 mL) were charged, and chlorosulfonyl isocyanate (8.6 g) was added dropwise at from 5 to 10° C. and reacted at the same temperature for 3 hours.

Step 2
Water (30 mL) was added dropwise to the obtained reaction liquid at from 5 to 10° C., followed by reaction for 30 minutes. Then, the reaction liquid was neutralized with solid NaOH (7.2 g) and then dichloromethane was distilled off. NaOH (4.8 g) was added and reacted at 100° C. for 3 hours.

To the obtained reaction liquid after hydrolysis, water (12 mL) was added and then concentrated hydrochloric acid was added to adjust the reaction liquid to pH 2 or lower. The obtained slurry was subjected to filtration, washed with water and dried to obtain desired product (amount obtained: 7.9 g, purity: 97.1%, yield: 90.1%, isomer ratio 3-MTCA:4-MTCA=99.0:1.0).

Example 2

Step 1 was carried out in the same manner as in Step 1 in Example 1.
Step 2 was carried out in the same manner as in Step 2 in Example 1 except that a 48 wt % aqueous NaOH solution (25.8 g) was used instead of NaOH, the amount of water added to the reaction liquid was changed from 30 mL to 12 mL, and the amount of water added to the reaction liquid after hydrolysis was changed from 12 mL to 18 mL to obtain a desired product (amount obtained: 7.7 g, purity: 98.2%, yield: 88.0%, isomer ratio 3-MTCA:4-MTCA=99.4:0.6).

Example 3

Step 1 was carried out in the same manner as in Step 1 in Example 1 except that 3-MT (17.7 g), dichloromethane (70 mL) and chlorosulfonyl isocyanate (26.4 g) were used.
Step 2 was carried out in the same manner as in Example 1 except that water (53.1 mL) and then a 48 wt % aqueous NaOH solution (76.5 g) were used.

To the reaction liquid after hydrolysis, methanol (53 mL) was added and then concentrated hydrochloric acid was added to adjust the reaction liquid to pH 2 or lower. Then, water (89 mL) was added, and the slurry was subjected to filtration, washed with water and dried to obtain a desired product (amount obtained: 23.8 g, purity: 95.8%, yield: 89%, isomer ratio 3-MTCA:4-MTCA=99.9:0.1).

Example 4

Step 1 was carried out in the same manner as in Step 1 in Example 1 except that 3-MT (17.7 g), toluene (70 mL) and chlorosulfonyl isocyanate (26.8 g) were used.
Step 2 was carried out in the same manner as in Example 1 except that water (52.1 mL) and then a 48 wt % aqueous NaOH solution (67.7 g) were used.

To the obtained reaction liquid after hydrolysis, methanol (35 mL) was added and then concentrated hydrochloric acid was added to adjust the reaction liquid to pH 2 or lower. Then, water (104 mL) was added, and the slurry was subjected to filtration, washed with water and dried to obtain a desired product (amount obtained: 23.9 g, purity: 97.7%, yield: 92.6%, isomer ratio 3-MTCA:4-MTCA=99.9:0.1).

Example 5

Step 1 was carried out in the same manner as in Step 1 in Example 1 except that 3-MT (17.7 g), methyl ethyl ketone (70 mL) and chlorosulfonyl isocyanate (26.8 g) were used.
Step 2 was carried out in the same manner as in Example 1 except that water (52.0 mL) and then a 48 wt % aqueous NaOH solution (70.1 g) were used.

To the obtained reaction liquid after hydrolysis, methanol (35 mL) was added and then concentrated hydrochloric acid was added to adjust the reaction liquid to pH 2 or lower. Then, water (88 mL) was added, and the slurry was subjected to filtration, washed with water and dried to obtain a desired product (amount obtained: 21.8 g, purity: 98.6%, yield: 85.6%, isomer ratio 3-MTCA:4-MTCA=99.9:0.1).

Example 6

Step 1 was carried out in the same manner as in Step 1 in Example 1 except that 3-MT (17.7 g), ethyl acetate (70 mL) and chlorosulfonyl isocyanate (26.8 g) were used.

Step 2 was carried out in the same manner as in Example 1 except that water (52.1 mL) and then a 48 wt % aqueous NaOH solution (78.6 g) were used.

To the obtained reaction liquid after hydrolysis, methanol (35 mL) was added and then concentrated hydrochloric acid was added to adjust the reaction liquid to pH 2 or lower. Then, water (106 mL) was added, and the slurry was subjected to filtration, washed with water and dried to obtain a desired product (amount obtained: 22.5 g, purity: 98.1%, yield: 87.8%, isomer ratio 3-MTCA:4-MTCA=99.9:0.1).

Example 7

Step 1
Into a four-necked flask equipped with a stirrer, a thermometer, a condenser tube and a dropping funnel, chlorosulfonyl isocyanate (75.7 g) and xylene (85 g) were charged, and then 3-MT (50.0 g) was added dropwise at from 5 to 10° C., followed by reaction at the same temperature for 2 hours to obtain (3-methyl-2-thiophenecarbonyl)sulfamoyl chloride.

Step 2
Water (147 mL) was added dropwise to the obtained reaction liquid at 40° C. or lower, followed by reaction at 40° C. for one hour to obtain 3-methyl-2-thiophenecarboxamide. A 48 wt % aqueous NaOH solution (193.4 g) was added to the reaction liquid, followed by heating to 100° C., and xylene was distilled off. Then, reaction was carried out at 100° C. for 3 hours.

To the obtained reaction liquid after hydrolysis, water (245 mL) and methanol (77 mL) were added and then concentrated hydrochloric acid was added to adjust the reaction liquid to pH 2.5 or lower, followed by stirring for one hour. The obtained slurry was subjected to filtration, washed with water, dried and suspended in 294 g of water, followed by stirring at 40° C. for one hour. The obtained slurry was subjected to filtration, washed with water and dried to obtain a desired product (3-MTCA) (amount obtained: 68.0 g, purity: 96.9%, yield: 93.9%, isomer ratio 3-MTCA:4-MTCA=99.9:0.1).

Example 8

Step 1
Into a four-necked flask equipped with a stirrer, a thermometer, a condenser tube and a dropping funnel, chlorosulfonyl isocyanate (88.7 g) and dibutyl ether (100 mL) were charged, 3-MT (57.9 g) was added dropwise at from 5 to 10° C. over a period of from about 70 to about 80 minutes, and further 100 mL of dibutyl ether was added, followed by reaction at the same temperature for 2 hours. From the reaction rate and HPLC-PA of 3-MT, disappearance (1% or lower) of 3-MT was confirmed.

Step 2
Water (147 mL) was added dropwise to the obtained reaction liquid at 40° C. or lower, followed by reaction at 40° C. for one hour. Then, a 48 wt % aqueous NaOH solution (224 g) was added to the reaction liquid, followed by heating to 100° C., and dibutyl ether was distilled off. Then, reaction was carried out at 100° C. for 3 hours.

To the obtained reaction liquid after hydrolysis, water (225 mL) and methanol (105 mL) were added, and then concentrated hydrochloric acid was added to adjust the reaction liquid to pH 2.5 or lower, followed by stirring for one hour. The obtained slurry was subjected to filtration, washed with water, dried and suspended in 294 g of water, followed by stirring at 40° C. for one hour. The obtained slurry was subjected to filtration, washed with water and dried to obtain a desired product (amount obtained: 79.8 g, purity: 96.6%, yield: 91.2%, isomer ratio 3-MTCA:4-MTCA=99.0:1.0).

The reaction liquid was analyzed by high performance liquid chromatography (HPLC) in Examples 1 to 8, and the results are shown in Tables 1 and 2. In Tables 1 and 2, "sulfonamide" represents (3-methyl-2-thiophenecarbonyl) sulfamoyl chloride, "amide" 3-methyl-2-thiophenecarboxamide, and HPLC-PA (%) the peak area ratio (peak area %). HPLC measurement conditions are as follows.

Column: Inertsil ODS-3 (tradename, manufactured by GL Sciences Inc., particle size: 3 μm, inner diameter: 4.6 mm, length: 250 mm)
Mobile phase: acetonitrile/water/phosphoric acid=2,000 mL/1,000 mL/1 g
Column temperature: 40° C.
Flow rate: 1.0 mL/min
Detection: 240 nm (Step 1), 254 nm (Step 2)

TABLE 1

| | | HPLC-PA (%) | | | |
|---|---|---|---|---|---|
| | | 3-MT | Sulfonamide | Amide | 3-MTCA |
| Example 1 | Step 1 | 0.2 | 99.1 | 0.6 | — |
| | Step 2 | 0 | 0 | 0.5 | 99.3 |
| Example 2 | Step 1 | 2.1 | 95.1 | 2.4 | — |
| | Step 2 | 0 | 0 | 0.5 | 99.3 |
| Example 3 | Step 1 | 0.8 | 97.0 | 0 | — |
| | Step 2 | 0 | 0 | 0.4 | 99.4 |
| Example 4 | Step 1 | 0.8 | 94.1 | 0 | — |
| | Step 2 | 0 | 0 | 0.6 | 99.1 |
| Example 5 | Step 1 | 4.5 | 87.0 | 0.5 | — |
| | Step 2 | 0 | 0 | 0.3 | 99.5 |
| Example 6 | Step 1 | 0.2 | 89.8 | 0 | — |
| | Step 2 | 0 | 0 | 0.6 | 99.1 |

TABLE 2

| | | HPLC-PA (%) | | | |
|---|---|---|---|---|---|
| | | 3-MT | Sulfonamide | Amide | 3-MTCA |
| Example 7 | Step 1 | 0.4 | 98.9 | 0 | — |
| | Step 2 | 0 | 0 | 0.5 | 99.4 |
| Example 8 | Step 1 | 0.2 | 93.2 | 0.8 | — |
| | Step 2 | 0 | 0 | 0.1 | 99.0 |

As evident from HPLC-PA (%) in Tables 1 and 2, according to the method of the present invention, the ratios of peaks other than the peak of the desired product are very low and the content of impurities is very low, thus indicating that a high purity desired product can be obtained with high yield.

Comparative Example 1

Into an autoclave equipped with a stirrer, 3-MT (5.9 g) and toluene (33 mL) were charged, and a 25% ethyl aluminum dichloride/toluene solution (30.5 g) was added dropwise at from 20 to 30° C. After dropwise addition, under pressure to 3.0 MPa by carbon dioxide, reaction was carried out at 100° C. for 3 hours. The obtained reaction liquid was added to ice water (57 mL), and the interior of the autoclave was washed with toluene (12 mL). Concentrated hydrochloric acid (10.8 g) was dropwise added, followed by heating to 57° C., and the aqueous layer was removed by liquid separation. An 8 wt % aqueous NaOH solution (29.5 g) was added to the organic layer, followed by stirring for one hour, and the organic layer was removed by liquid separation. Concentrated hydrochloric acid (6.2 g) was added to the obtained aqueous layer to adjust the reaction liquid to pH 2 or lower. The obtained slurry was subjected to filtration, washed with water and dried to obtain a desired product (amount obtained: 7.7 g, purity: 74.3%, yield: 67.1%, isomer ratio 3-MTCA:4-MTCA=95.8:4.2).

In the reaction solution in Comparative Example 1, a tarry component was confirmed, which was estimated to result from use of a Lewis acid.

Comparative Example 2

Into a four-necked flask equipped with a stirrer, a thermometer, a condenser tube and a dropping funnel, 3-MT (5.9 g) and dichloromethane (30 mL) were charged, and p-toluenesulfonyl isocyanate (12.5 g) was added dropwise at from 5 to 10° C., followed by reaction at the same temperature for 3 hours and then at room temperature for 15 hours.

The reaction was tracked by high performance liquid chromatography, whereupon about 80% (HPLC-PA value) of the raw material 3-MT remained even after the reaction at room temperature for 15 hours, and the reaction was very slow as compared with the method of the present invention.

Comparative Example 3 (Method in WO2016/161063)

Step 1

Into a four-necked flask equipped with a stirrer, a thermometer, a condenser tube and a dropping funnel, non-substituted thiophene (50.0 g) and dibutyl ether (100 mL) were charged, chlorosulfonyl isocyanate (88.7 g) was added dropwise at from 5 to 10° C. over a period of from about 70 to about 80 minutes, and further 100 mL of dibutyl ether was added, followed by reaction at the same temperature for 3 hours. The reaction was tracked by high performance liquid chromatography, whereupon about 30.7% (HPLC-PA value) of the raw material non-substituted thiophene remained even after reaction further for 2 hours (5 hours after completion of dropwise addition), and the reaction was very slow as compared with the method of the present invention. 100 mL of dibutyl ether was further added, followed by reaction at the same temperature for 24 hours, however, (2-thiophenecarbonyl)sulfamoyl chloride was obtained only in an amount of 68% (HPLC-PA value).

Step 2

Water (170 mL) was added dropwise to the obtained reaction liquid at 40° C. or lower, followed by reaction at 40° C. for one hour. Then, a 48 wt % aqueous NaOH solution (224 g) was added to the reaction liquid, followed by heating to 100° C., and dibutyl ether was distilled off. Then, reaction was carried out at 100° C. for 4 hours. To the obtained reaction liquid after hydrolysis, water (220 mL) and methanol (88 mL) were added, and concentrated hydrochloric acid was added to adjust the reaction liquid to pH 2.5 or lower, followed by stirring for one hour. The obtained slurry was subjected to filtration, washed with water, dried and suspended in 294 g of water, followed by stirring at 40° C. for one hour. The obtained slurry was subjected to filtration, washed with water and dried to obtain 2-thiophenecarboxylic acid (amount obtained: 52.6 g, purity: 98.1%, yield: 68.2%).

INDUSTRIAL APPLICABILITY

According to the production method of the present invention, 3-methyl-2-thiophenecarboxylic acid useful as an intermediate for producing drugs and agrochemicals can be produced easily and efficiently with high yield and high selectivity.

The entire disclosure of Japanese Patent Application No. 2016-209484 filed on Oct. 26, 2016 including specification, claims and abstract is incorporated herein by reference in its entirety.

The invention claimed is:

1. A method for producing 3-methyl-2-thiophenecarboxylic acid comprising:
    reacting (1) 3-methylthiophene with chlorosulfonyl isocyanate to obtain a first reaction product, and
    hydrolyzing (2) the first reaction product to obtain the 3-methyl-2-thiophenecarboxylic acid,
    wherein the reacting (1) is carried out at from 0 to 20° C.

2. The method according to claim 1, wherein the hydrolyzing (2) comprises:
    treating (2-1) the first reaction product with water; wherein in the treating (2-1), a second reaction product is obtained; and
    treating (2-2) the second reaction product with a base; wherein in the treating (2-2), the 3-methyl-2-thiophenecarboxylic acid is obtained.

3. The method according to claim 1, wherein the reacting (1) is carried out in the presence of a first solvent.

4. The method according to claim 3, wherein the first solvent is at least one selected from the group consisting of dichloromethane, 1,2-dichloroethane, chlorobenzene, toluene, xylene, ethyl acetate, dibutyl ether, and methyl ethyl ketone.

5. The method according to claim 1, wherein the hydrolyzing (2) is carried out in the presence of a second solvent.

6. The method according to claim 5, wherein the second solvent is at least one selected from the group consisting of water, dichloromethane, chlorobenzene, toluene, xylene, dibutyl ether, and tetrahydrofuran.

7. The method according to claim 2, wherein the treating (2-1) is carried out at from 0 to 50° C.

8. The method according to claim 2, wherein the treating (2-2) is carried out at from 80 to 120° C.

9. The method according to claim 7, wherein the treating (2-2) is carried out at from 80 to 120° C.

10. The method according to claim 2, wherein the base is sodium hydroxide.

11. The method according to claim 7, wherein the base is sodium hydroxide.

12. The method according to claim 9, wherein the base is sodium hydroxide.

* * * * *